(12) United States Patent
Karst et al.

(10) Patent No.: US 9,162,065 B2
(45) Date of Patent: Oct. 20, 2015

(54) SYSTEMS AND METHODS FOR ESTIMATING CENTRAL ARTERIAL BLOOD PRESSURE OF A PATIENT

(71) Applicant: PACESETTER, INC., Sylmar, CA (US)

(72) Inventors: Edward Karst, Los Angeles, CA (US); Brian Jeffrey Wenzel, Morgan Hill, CA (US); Timothy A. Fayram, Gilroy, CA (US); Allen Keel, San Diego, CA (US); Wenbo Hou, Santa Clarita, CA (US); Taraneh Ghaffari Farazi, Santa Clara, CA (US); Jong Gill, Valencia, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 14/616,519

(22) Filed: Feb. 6, 2015

(65) Prior Publication Data
US 2015/0151130 A1 Jun. 4, 2015

Related U.S. Application Data

(63) Continuation of application No. 13/033,465, filed on Feb. 23, 2011, now abandoned.

(51) Int. Cl.
| | |
|---|---|
| A61B 5/02 | (2006.01) |
| A61N 1/365 | (2006.01) |
| A61B 5/021 | (2006.01) |
| A61B 5/0215 | (2006.01) |
| A61B 5/0452 | (2006.01) |
| A61N 1/39 | (2006.01) |

(52) U.S. Cl.
CPC ........ *A61N 1/36585* (2013.01); *A61B 5/02125* (2013.01); *A61B 5/02154* (2013.01); *A61B 5/0452* (2013.01); *A61N 1/3962* (2013.01); *A61N 1/3987* (2013.01); *A61N 1/36564* (2013.01)

(58) Field of Classification Search
CPC .................................................... A61B 5/0215
See application file for complete search history.

(56) References Cited

U.S. PATENT DOCUMENTS

| | | | | |
|---|---|---|---|---|
| 2002/0087087 | A1* | 7/2002 | Oka et al. ....................... | 600/485 |
| 2009/0062667 | A1* | 3/2009 | Fayram et al. ................. | 600/486 |

OTHER PUBLICATIONS

Pulse Wave Analysis and Pulse Wave Velocity—A Review of Blood Pressure Interpretation 100 Years After Korotkov by Hirata et al., Circulation, vol. 70, pp. 1231-1239, 2006.*

* cited by examiner

*Primary Examiner* — Patricia Mallari
*Assistant Examiner* — Vasuda Ramachandran

(57) ABSTRACT

In specific embodiments, a method for estimating central arterial blood pressure (CBP), comprises determining a time $t_1$ from a predetermined feature of a signal indicative of electrical activity to a predetermined feature of one of a first and second signals, the time $t_1$ being a first pulse arrival time ($PAT_1$) indicative of how long it takes a pulse wave to travel from the aorta to one of a first and second sites, determining a time $t_2$, the time $t_2$ being a second pulse arrival time ($PAT_2$) indicative of how long it takes a pulse wave to travel from the aorta to the other of the first and second sites, and (f) estimating the patient's central arterial blood pressure (CBP) based on the first pulse arrival time ($PAT_1$) and the second pulse arrival time ($PAT_2$).

19 Claims, 8 Drawing Sheets

US 9,162,065 B2

SYSTEMS AND METHODS FOR ESTIMATING CENTRAL ARTERIAL BLOOD PRESSURE OF A PATIENT

CROSS REFERENCE TO RELATED APPLICATIONS

This application is a continuation of U.S. patent application Ser. No. 13/033,465, filed Feb. 23, 2011.

BACKGROUND

Peripheral arterial blood pressure is a metric of blood pressure that is routinely, and easily measured using a cuff, for example. However, compliance of large arteries and resistance of small arteries, arterioles and capillaries are two major properties of the vasculature that influence arterial blood pressure. Depending on these factors, peripheral arterial blood pressure measured with a cuff may differ significantly from central blood pressure in the aorta and largest arteries. In particular, the velocity and location of pressure wave reflections may lead to individual and unpredictable differences between central arterial blood pressure, which is the afterload experienced by the left ventricle, and the peripheral pressure present in the arterial microvasculature. Central arterial blood pressure is regarded as an important indicator of cardiovascular health, and a blood pressure sensor that separately estimates central and peripheral arterial blood pressure could have significant clinical value for patients with various disease states being treated with a variety of therapies. However, central arterial blood pressure is not currently measureable by non-invasive or minimally invasive techniques

SUMMARY

Embodiments of the present invention are related to implantable systems and methods for use therewith for estimating central arterial blood pressure of a patient. In accordance with an embodiment, a method for estimating a patient's central arterial blood pressure (CBP) includes using an implanted sensor at a first site to obtain a first signal indicative of changes in arterial blood volume at the first site (the first site being along one or more peripheral arterial structures of the patient), using an implanted sensor at a second site to obtain a second signal indicative of changes in arterial blood volume at the second site (the second site being a distance from the first site downstream along an arterial path of the one or more peripheral arterial structures of the patient), and using implanted electrodes to obtain a signal indicative of electrical activity of the patient's heart.

A time $t_1$ is determined from a predetermined feature of the signal indicative of electrical activity to a predetermined feature of one of the first and second signals, the time $t_1$ being a first pulse arrival time ($PAT_1$) indicative of how long it takes a pulse wave to travel from the patient's aorta to one of the first and second sites. A time $t_2$ is determined from a predetermined feature of the signal indicative of electrical activity to a predetermined feature of the other of the first and second signals, the time $t_2$ being a second pulse arrival time ($PAT_2$) indicative of how long it takes a pulse wave to travel from the patient's aorta to the other of the first and second sites. The patient's central arterial blood pressure (CBP) is estimated based on the first pulse arrival time ($PAT_1$) and the second pulse arrival time ($PAT_2$).

In an embodiment, the first pulse arrival time (PAT1), the second pulse arrival time (PAT2) and the distance from the first site to the second site are used to estimate a peripheral pulse wave velocity (PPWV), which is indicative of a pulse wave velocity between the first and second sites. A central pulse wave velocity (CPWV), indicative of a pulse wave velocity proximal the patient's aorta, is estimated based on the first pulse arrival time ($PAT_1$) and the peripheral pulse wave velocity (PPWV). The patient's central arterial blood pressure (CBP) is estimated based on the estimated central pulse wave velocity (CPWV). For example, the central pulse wave velocity (CPWV) can be estimated using the following equation:

$$v_{cpw} \approx \frac{v_{ppw} * d_c}{v_{ppw} * PAT_x - d_p}$$

where $v_{cpw}$ is the estimated central pulse wave velocity (CPWV), $v_{ppw}$ is the estimated peripheral pulse wave velocity (PPWV), $d_c$ is a distance traveled in large arteries (also referred to herein as central arterial structures), $PAT_x$ can be $PAT_1$ or $PAT_2$, and $d_p$ is the distance traveled in small arteries and arterioles (also referred to herein as peripheral arterial structures) to the site where $PAT_x$ is obtained (i.e., either the first site or the second site). The distances $d_c$ and $d_p$ can be obtained from a calculation based on patient anatomy.

In an embodiment, the central arterial blood pressure (CBP) is estimated based on the square of the central pulse wave velocity (CPWV). For example, the central arterial blood pressure (CBP) can be estimated using the equation:

$$CBP \approx k1 * v_{cpw}^2 + k2,$$

where CBP is the estimated central arterial blood pressure, $v_{cpw}$ is the estimated central pulse wave velocity (CPWV), k1 is a constant indicative of a linearized scaling factor between pulse wave velocity and blood pressure, and k2 is a constant indicative of an offset used with the scaling factor to make a linear approximation of blood pressure based on pulse wave velocity.

The constants k1 and k2 can be determined in the following manner. While the patient is in an initial position, a secondary technique is used to measure initial peripheral blood pressure of the patient, using the implanted sensor at the first site to obtain a first calibration signal indicative of a change in arterial blood volume, and using the implanted sensor at the second site to obtain a second calibration signal indicative of a change in blood volume. While the patient is in a secondary position, the secondary technique is used to measure a secondary peripheral blood pressure of the patient, using the implanted sensor at the first site to obtain a third calibration signal indicative of a change in arterial blood volume, and using the implanted sensor at the second site to obtain a fourth calibration signal indicative of a change in blood volume. The constants k1 and k2 are calculated using the first calibration signal, the second calibration signal, the third calibration signal, the fourth calibration signal, the initial peripheral blood pressure, the secondary peripheral blood pressure, and the distance from the first site to the second site.

In an embodiment, peripheral arterial blood pressure (PBP) can be estimated based on the square of the peripheral pulse wave velocity (PPWV). For example, peripheral arterial blood pressure (PBP) can be estimated based on the following equation:

$$PBP \approx k3 * v_{ppw}^2 + k4,$$

where PBP is the estimated peripheral arterial blood pressure, $v_{ppw}$ is the estimated peripheral pulse wave velocity (PPWV), k3 is a constant indicative of a linearized scaling factor between pulse wave velocity and blood pressure (accounting for blood density, blood volume and vascular compliance), and k4 is a constant indicative of an offset used with the scaling factor to make a linear approximation of blood pressure based on pulse wave velocity.

The constants k3 and k4 can be determined in the following manner. While the patient is in an initial position, a secondary technique is used to measure initial peripheral blood pressure of the patient, using the implanted sensor at the first site to obtain a first calibration signal indicative of a change in arterial blood volume, and using the implanted sensor at the second site to obtain a second calibration signal indicative of a change in blood volume. While the patient is in a secondary position, the secondary technique is used to measure a secondary peripheral blood pressure of the patient, using the implanted sensor at the first site to obtain a third calibration signal indicative of a change in arterial blood volume, and using the implanted sensor at the second site to obtain a fourth calibration signal indicative of a change in blood volume. The constants k3 and k4 are calculated using the first calibration signal, the second calibration signal, the third calibration signal, the fourth calibration signal, the initial peripheral blood pressure, the secondary peripheral blood pressure, and the distance from the first site to the second site.

In an embodiment, the first signal indicative of changes in arterial blood volume at the first site is obtained using an implanted optical sensor at the first site to obtain a first photoplethysmography (PPG) signal indicative of changes in arterial blood volume at the first site. Similarly, the second signal indicative of changes in arterial blood volume at the second site can be obtained using an implanted optical sensor at the second site to obtain a second photoplethysmography (PPG) signal indicative of changes in arterial blood volume at the second site. In an embodiment, the signal indicative of electrical activity of the patient's heart is obtained using implanted electrodes to obtain an intracardiac electrogram (IEGM) signal indicative of electrical activity of the patient's heart.

In an embodiment, the predetermined features of the first and second PPG signals are selected from the group consisting of the minimum amplitude of the PPG signal, the maximum upward slope of the PPG signal, the maximum amplitude of the PPG signal, the maximum downward slope of the PPG signal prior to the dicrotic notch, the dicrotic notch of the PPG signal, and the maximum downward slope of the PPG signal following the dicrotic notch. In an embodiment, the predetermined feature of the IEGM signal is selected from the group consisting of a Q-wave, an R-wave, and a QRS complex.

As mentioned above, embodiments of the present invention are also directed to systems for estimating a patient's central arterial blood pressure (CBP). Such a system can include a first sensor arrangeable at a first site to obtain a first signal indicative of changes in arterial blood volume at the first site (the first site being along one or more peripheral arterial structures of the patient), a second sensor arrangeable at a second site to obtain a second signal indicative of changes in arterial blood volume at the second site (the second site being a distance from the first site downstream along an arterial path of the one or more peripheral arterial structures of the patient), one or more electrodes implantable to obtain a signal indicative of electrical activity of the patient's heart, and a monitor adapted to estimate the patient's central arterial blood pressure (CBP) based on the signal indicative of electrical activity, the first signal and the second signal.

In an embodiment, the monitor is adapted to determine a time t1 from a predetermined feature of the signal indicative of electrical activity to a predetermined feature of one of the first and second signals, the time t1 being a first pulse arrival time (PAT1) indicative of how long it takes a pulse wave to travel from the patient's aorta to one of the first and second sites. The monitor is also adapted to determine a time t2 from a predetermined feature of the signal indicative of electrical activity to a predetermined feature of the other of the first and second signals, the time t2 being a second pulse arrival time (PAT2) indicative of how long it takes a pulse wave to travel from the patient's aorta to the other of the first and second sites. The monitor is adapted to estimate the patient's central arterial blood pressure (CBP) based on the first pulse arrival time (PAT1) and the second pulse arrival time (PAT2), e.g., using similar techniques to those described above.

This summary is not intended to summarize all of the embodiments of the present invention. Further and alternative embodiments, and the features, aspects, and advantages of the embodiments of invention will become more apparent from the detailed description set forth below, the drawings and the claims.

DETAILED DESCRIPTION

Figure 1A:
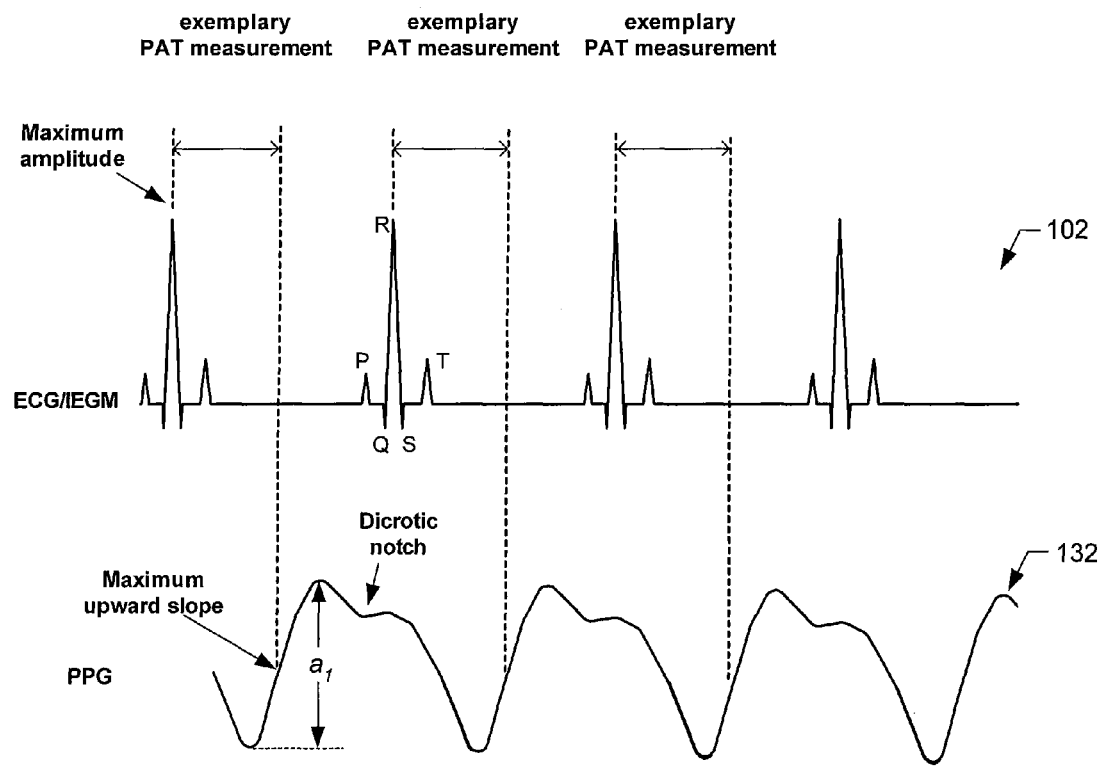
FIG. 1A includes exemplary signal waveforms that are used to show the relative timing of an electrocardiogram (ECG) signal (or intracardiac electrogram (IEGM) signal) and a photoplethysmography (PPG) signal, and how an exemplary pulse arrival time (PAT) measurement can be determined in accordance with an embodiment of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Central arterial blood pressure can be defined as pressure within the blood vessels proximate to the heart, e.g., the aorta. For the purposes of this description, and for embodiments of methods and systems in accordance with the present invention, central arterial blood pressure is assumed to be approximately uniform throughout large blood vessels carrying blood pumped from the heart. As the large blood vessels branch into small blood vessels downstream from the aorta, such as the arterioles and capillaries, reflection of pulse waves along the blood vessels cause pulse amplification which typically results in higher systolic blood pressure. A distinction can be made, therefore, between the large blood vessels, which are referred to herein as central arterial structures, and small blood vessels, which are referred to herein as peripheral arterial structures.

Central arterial blood pressure is considered an important indicator of cardiovascular health, and reflects the afterload that must be overcome by the left ventricle to deliver blood to the systemic circulation. Direct measurement of central arterial blood pressure requires placing an invasive catheter in the aorta. Peripheral arterial blood pressure is routinely and easily measured, for example using a sphygmomanometer, which is a blood pressure meter that relies on an inflatable cuff. Compliance of large arteries and resistance of small arteries, arterioles, and capillaries are two major properties of the vasculature that influence arterial blood pressure. These properties can vary from patient to patient due to a number of factors including but not limited to diet, exercise, age, genetics, and whether a patient smokes. Patient treatment is currently based on incomplete information because central arterial blood pressure cannot be reliably extrapolated from peripheral arterial blood pressure.

Embodiments of systems and methods in accordance with the present invention can be applied to estimate a patient's central arterial blood pressure (CBP) base on a pair of pulse arrival time (PAT) measurements. One of the PAT measurements is obtained from a peripheral arterial structure at a first location, and the other of the PAT measurements is obtained from a peripheral arterial structure at a second location a known distance downstream from the first location (i.e., blood expelled from the left ventricle passes the first location before it reaches the second location).

Referring to FIG. 1A, the representative signal waveforms therein are used to show the relative timing of electrical and mechanical cardiac events that occur during cardiac cycles. The upper most waveform is representative of an electrocardiogram (ECG) or intracardiac electrogram (IEGM) signal 102 (collectively referred to as an ECG/IEGM signal), which is indicative of electrical activity of the patient' heart. The lower waveform is representative of a photoplethysmograph (PPG) or impedance plethysmograph (IPG) signal 132, both of which are indicative of changes in arterial blood volume remote from the patient's heart. The PPG or IPG signal 132 (collectively referred to as PPG/IPG signal 132) is indicative of mechanical activity of the patient's heart because the PPG/IPG signal 132 represents changes in the flow of blood through the vessels probed by the PPG/IPG sensor (or stated another way, changes in arterial blood volume), which is dependent on the mechanical activity of the heart.

Referring to the ECG/IEGM signal 102, each cycle of the signal 102 is shown as including a P wave, a QRS complex (including Q, R and S waves) and a T wave. The P wave is caused by depolarization of the atria. This is followed by atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole.

Figure 1B:
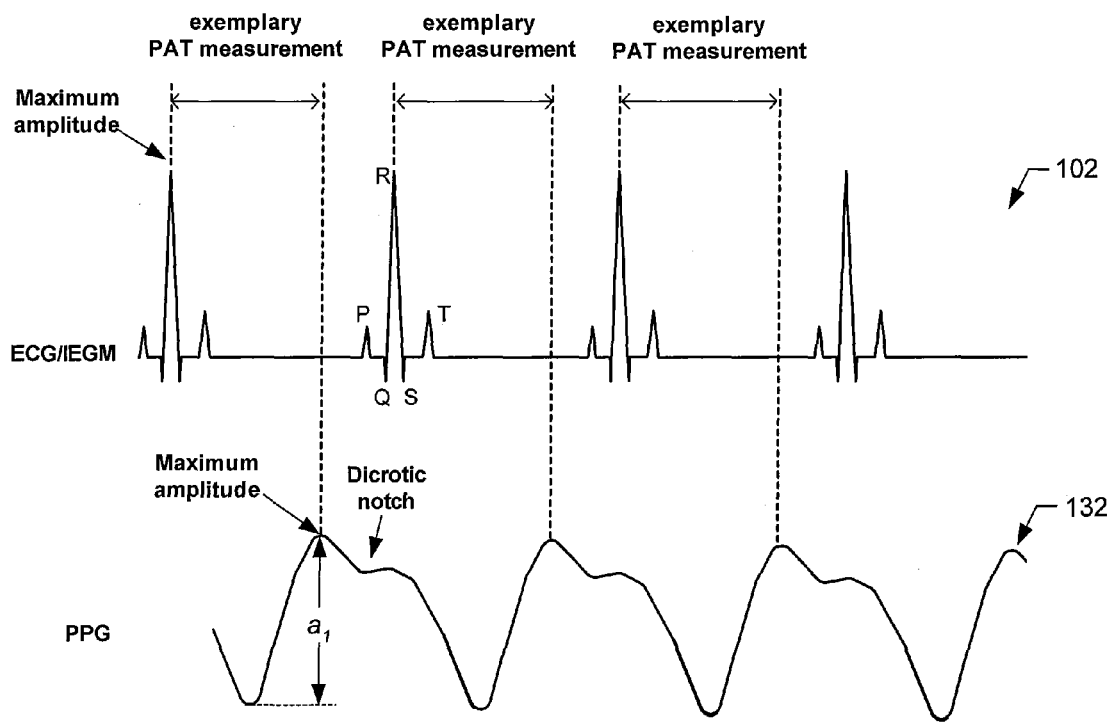
FIG. 1B includes the same exemplary signal waveforms shown in FIG. 1A, but shows how another exemplary PAT measurement can be determined in accordance with an embodiment of the present invention.

An exemplary PAT measurement is also shown in FIG. 1A. In general, a PAT measurement can be determined, in accordance with embodiments of the present invention, by determining a time from a detected predetermined feature of an ECG/IEGM (e.g., 102) to a detected predetermined feature of the signal indicative of changes in arterial volume, which can be a PPG or IPG signal (e.g., 132), but is not limited thereto. In FIG. 1A, the predetermined feature of the ECG/IEGM signal is the maximum amplitude of the R wave, and the predetermined feature of the PPG/IPG signal is the maximum upward slope. In other words, the PAT measurement can be determined by determining a time from the maximum amplitude of the R wave 102 to the maximum upward slope of the PPG/IPG signal 132, as illustrated in FIG. 1A. Alternatively, as illustrated in FIG. 1B, the PAT measurement can be determined using some other feature of one or both of the ECG/IEGM and PPG/IPG signals, for example, by determining a time from the maximum amplitude of the R wave of the ECG/IEGM signal 102 to the maximum amplitude of the PPG/IPG signal 132 prior to the dicrotic notch. These are just a few examples, which are not meant to be limiting. Alternative predetermined features of the ECG/IEGM signal can be used, as can alternative predetermined features of the PPG/IPG signal.

Figure 2:
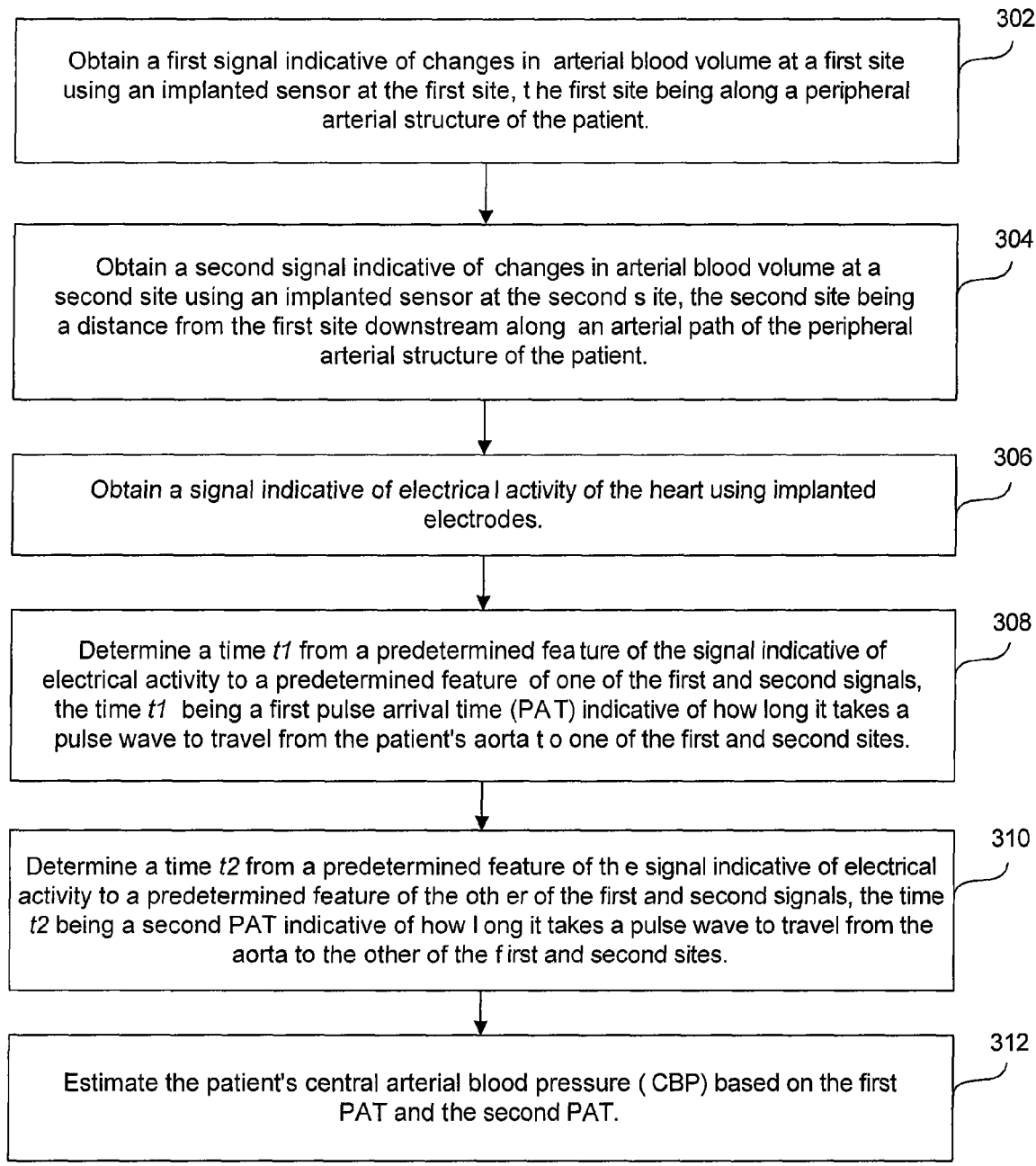
FIG. 2 is a flow diagram of a method for estimating a patient's central arterial blood pressure in accordance with an embodiment of the present invention.

FIG. 2 is a flow diagram for an embodiment of a method of estimating a patient's central arterial blood pressure (CBP) in accordance with the present invention. A first signal indicative of changes in arterial blood volume is obtained at a first site using an implanted sensor (Step 302). The first site is located at a peripheral arterial structure of the patient. A second signal indicative of changes in arterial blood volume is obtained at a second site using an implanted sensor (Step 304). The second site is located a known distance downstream from the first site at a peripheral arterial structure of the patient. The terms upstream and downstream refer to the relative arrangement of sites along an arterial blood flow path, wherein a downstream site is located further away from the central aorta along the arterial blood flow path. The peripheral arterial structure of the first site need not necessarily be the same peripheral arterial structure of the second site. For example, two closely spaced arterioles that are branched upstream from a common artery can have substantially the same blood flow characteristics. Further, a downstream site can be branched from an upstream site. Still further, a signal may be obtained from multiple, closely arranged structures such as capillary beds, for which a determination of PAT will be substantially consistent despite a variation in the individual structures.

In addition to the first and second signals indicative of changes in arterial blood volume, a signal indicative of electrical activity of the heart is obtained using one or more electrodes (Step 306). For example, as described in detail below, a signal indicative of electrical activity can be obtained using electrode(s) implanted within the heart. Alternatively, a signal indicative of electrical activity of the heart can be obtained percutaneously using electrodes externally applied along the patient's body. For example, a classic 12-lead ECG can be obtained using ten electrodes comprising a conducting gel embedded in the middle of a self-adhesive pad onto which cables clip.

As shown above in FIGS. 1A and 1B, a first PAT indicative of how long it takes a pulse wave to travel from the patient's aorta to one of the first and second sites is determined by determining a time from a predetermined feature of the signal indicative of electrical activity to a predetermined feature of the signal obtained at the one of the first and second sites (Step 308). A second PAT indicative of how long it takes a pulse wave to travel from the patient's aorta to the other of the first and second sites is determined by determining a time from a predetermined feature of the signal indicative of electrical activity to a predetermined feature of the signal obtained at the other of the first and second sites (Step 310). The patient's central arterial blood pressure can then be estimated based on the first PAT and the second PAT (Step 312).

An embodiment of a method in accordance with the present invention can be applied to estimate a patient's central arterial blood pressure (CBP) by estimating a central pulse wave velocity based on the first PAT and the second PAT. The central pulse wave velocity, $v_{cpw}$, can be estimated based on the peripheral pulse wave velocity, $v_{ppw}$, using the following equation:

$$v_{cpw} \approx \frac{d_c}{t_c}$$

where $d_c$ is a distance traveled in large arteries (also referred to herein as central arterial structures) and $t_c$ is the time that a pulse wave takes to travel through the central arterial structures. The time, $t_c$, can be estimated as a portion of the total time that a pulse wave travels along a blood flow path to a point of measurement at a peripheral arterial structure. The total time measured at a peripheral arterial structure comprises both $t_c$ and the time, $t_p$, that a pulse wave takes to travel through the peripheral arterial structures to the point of measurement. Thus, the time, $t_c$, can be estimated with the following equation:

$$t_c = PAT_x - t_p$$

where $PAT_x$ can be $PAT_1$ or $PAT_2$, and $t_p$ is determined to the location of $PAT_x$. The time, $t_p$, can be estimated with the following equation:

$$t_p \approx \frac{d_p}{v_{ppw}}$$

where $d_p$ is the distance traveled in small arteries and arterioles (also referred to herein as peripheral arterial structures) to the site where $PAT_x$ is obtained (i.e., either the first site or the second site), and $v_{ppw}$ is the peripheral pulse wave velocity. While, embodiments described herein approximate the arteries as divided into a single segment at a central arterial pressure (having a length equivalent to distance, $d_c$) and another segment at a peripheral pressure (having a length equivalent to distance, $d_p$), the pressure actually evolves continuously and is approximated by the piecewise separation.

The peripheral pulse wave velocity, $v_{ppw}$, can be calculated using the following equation:

$$v_{ppw} = \frac{\delta}{PAT_2 - PAT_1}$$

where $\delta$ is the known distance between the first site and the second site at which signals indicative of changes in arterial blood volume are obtained. $PAT_1$ is indicative of the time it takes a pulse wave to travel from the patient's aorta to one of the first site and the second site and $PAT_2$ is indicative of the time it takes a pulse wave to travel from the patient's aorta to the other of the first site and the second site.

Substituting for $t_c$ and $t_p$ allows central pulse wave velocity, $v_{cpw}$, to be estimated based on the calculable peripheral pulse wave velocity, $v_{ppw}$, using the following equation:

$$v_{cpw} \approx \frac{v_{ppw} * d_c}{v_{ppw} * PAT_x - d_p}$$

Notably, the absolute and/or relative distances, $d_p$ and $d_c$, that a pulse wave travels along the blood flow path, are unknowns. In an embodiment, estimates for $d_p$ and $d_c$ can be obtained from physiologic estimations based, for example, on information such as gender, height, and weight compiled in tables, charts, or other databases. The physiologic estimations may be obtained empirically, through calculations or results based on previous anatomic studies of the circulatory system, or through any other technique that can provide generally quantifiable results.

A patient's central arterial blood pressure (CBP) can be estimated based on the estimated central pulse wave velocity, $v_{cpw}$, using the equation:

$$CBP \approx k1 * v_{cpw}^2 + k2$$

where k1 is a constant indicative of a linearized scaling factor between pulse wave velocity and blood pressure, and k2 is a constant indicative of an offset used with the scaling factor to make a linear approximation of blood pressure based on pulse wave velocity.

The constants, k1 and k2, can be determined, for example, by estimating central pulse wave velocity, $v_{cpw}$, with the patient assuming two different positions. Initial peripheral blood pressure of the patient is measured using a secondary technique, for example using an inflatable cuff, while the patient is in an initial position. Also, while the patient is in the initial position, a first calibration signal (e.g., a first PPG signal) indicative of a change in arterial blood volume is obtained at the first site using the implanted sensor, and a second calibration signal (e.g., a second PPG signal) indicative of a change in blood volume is obtained at the second site using the implanted sensor. The patient then assumes a secondary position and a secondary peripheral blood pressure of the patient is measured using the secondary technique (e.g., the inflatable cuff). While the patient is in the secondary position, a third calibration signal (e.g., a third PPG signal) indicative of a change in arterial blood volume is obtained at the first site using the implanted sensor, and a fourth calibration signal (e.g., a fourth PPG signal) indicative of a change in blood volume is obtained at the second site using the implanted sensor. The first and second calibration signals and the distance δ from the first site to the second site are used to obtain an initial estimate of central pulse wave velocity, while the third and fourth calibration signals and the distance δ from the first site to the second site are used to obtain a secondary estimate of central pulse wave velocity. Assuming that the central arterial blood pressure scales with the peripheral blood pressure from the initial position to the secondary position, the two unknown constants k1 and k2 can be estimated using an initial equation for CBP substituting the initial peripheral blood pressure and using the initial central pulse wave velocity and a secondary equation for CBP substituting the secondary peripheral blood pressure, and using the secondary central pulse wave velocity.

A patient's peripheral arterial blood pressure (PBP) can be estimated based on the estimated peripheral pulse wave velocity, $v_{ppw}$, using the equation:

$$PBP \approx k3 * v_{ppw}^2 + k4$$

where k3 is a constant indicative of a linearized scaling factor between pulse wave velocity and blood pressure, and k4 is a constant indicative of an offset used with the scaling factor to make a linear approximation of blood pressure based on pulse wave velocity.

The constants, k3 and k4, can be determined, for example, by estimating peripheral pulse wave velocity, $v_{ppw}$, with the patient assuming two different positions. Initial peripheral blood pressure of the patient is measured using a secondary technique, for example using an inflatable cuff, while the patient is in an initial position. While the patient is in the initial position, a first calibration signal (e.g., a first PPG signal) indicative of a change in arterial blood volume is obtained at the first site using the implanted sensor and a second calibration signal (e.g., a second PPG signal) indicative of a change in blood volume is obtained at the second site using the implanted sensor. The patient then assumes a secondary position and a secondary peripheral blood pressure of the patient is measured using the secondary technique, e.g., the inflatable cuff. A third calibration signal (e.g., a third PPG signal) indicative of a change in arterial blood volume is obtained at the first site using the implanted sensor and a fourth calibration signal (e.g., a fourth PPG signal) indicative of a change in blood volume is obtained at the second site using the implanted sensor. The two unknown constants k3 and k4 can be estimated by simultaneous solution at the two different positions of the equation relating peripheral pulse wave velocity and peripheral blood pressure.

The disclosed systems and methods of the present invention generally relate to systems and methods for estimating a patient's central arterial blood pressure (CBP) using PAT estimations for at least two locations, one of which is downstream (i.e., further away from the central aorta within the circulatory system) relative to the other. While it is possible and within the scope of the present invention to obtain useable electrical measurements of cardiac activity for use with techniques of the present invention in an external (i.e., non-implantable) system or a subcutaneously implantable system, embodiments of the present invention will be described with reference to a cardiac device implanted within a patient for cardiac treatment, for example such as an ICD or CRT-D.

Implantable System

Figure 3:
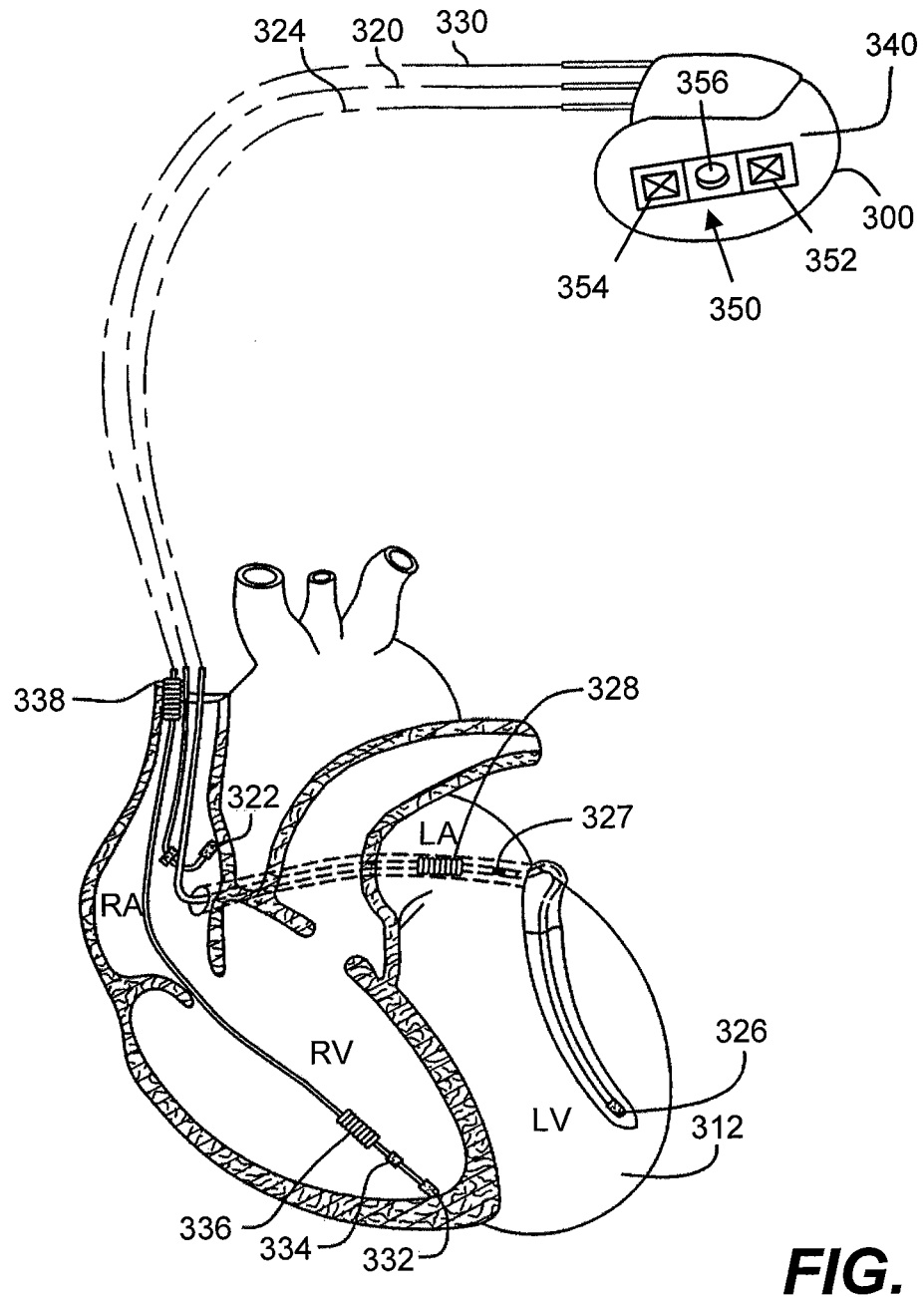
FIG. 3 illustrates an implantable system for determining central arterial blood pressure in accordance with an embodiment of the present invention.
Figure 4:
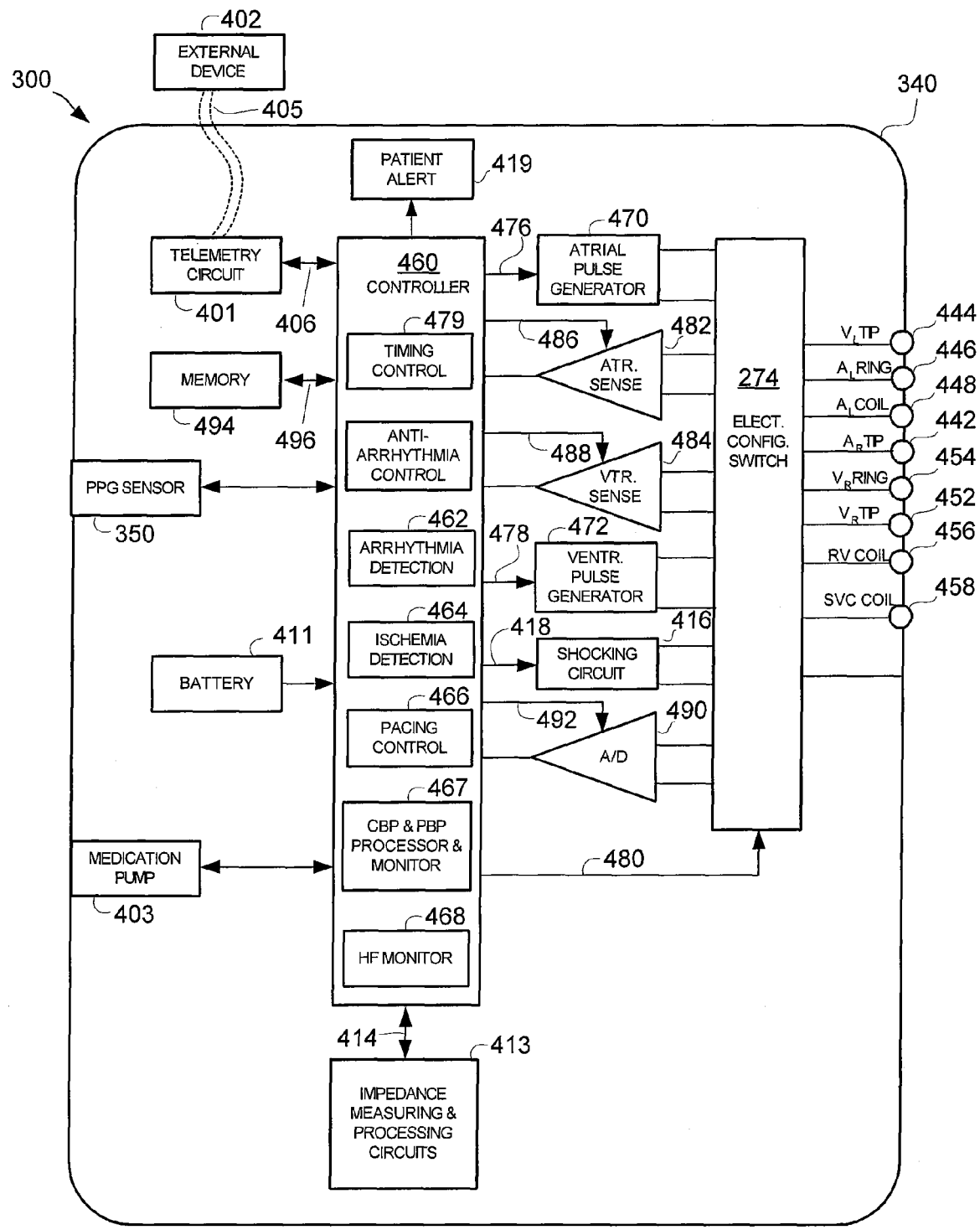
FIG. 4 is a simplified block diagram that illustrates possible components of the implantable device of the system shown in FIG. 3.

FIGS. 3 and 4 will now be used to describe an implantable system in accordance with an embodiment of the present invention that can be used to implement the above described techniques that estimate and/or monitor a patient's central arterial blood pressure. Referring to FIG. 3, the implantable system is shown as including an implantable stimulation device 300, which can be a pacing device and/or an implantable cardioverter defibrillator. The device 300 is shown as being in electrical communication with a patient's heart 312 by way of three leads, 320, 324, 330, which can be suitable for delivering multi-chamber stimulation and shock therapy. The leads can also be used to obtain IEGM signals, for use in embodiments of the present invention. As described below, it is also possible that one of these leads (or another lead) can include an optical sensor (also referred to as a PPG sensor) that is useful for obtaining a PPG signal, similar to signal 132 shown in FIG. 1A.

In FIG. 3, the implantable stimulation device 300 is shown as having a PPG sensor 350 (also referred to as an optical sensor) attached to its housing 340. The PPG sensor 350, which can be used to obtain a PPG signal similar to signal 132 shown in FIGS. 1A and 1B, includes a pair of light sources 352, 354 spaced apart a known distance and a light detector 356 arranged between the light sources. The light sources 352, 354 illuminate a target and can include one or more light emitted diodes (LEDs), laser diodes, organic light emitting diodes (OLEDs), liquid crystal display (LCD), bulbs or other light emitting structures. Each light source 352, 354 further can be a single or multi-wavelength light source. A multi-wavelength light source can include multiple light emitting devices each device emitting light at different wavelengths. The light detector 356 can include, e.g., at least one photoresistor, photodiode, phototransistor, photodarlington or avalanche photodiode for detecting reflected or absorbed light, but is not limited thereto. Light detectors are often also referred to as photodetectors or photocells.

Figure 5:
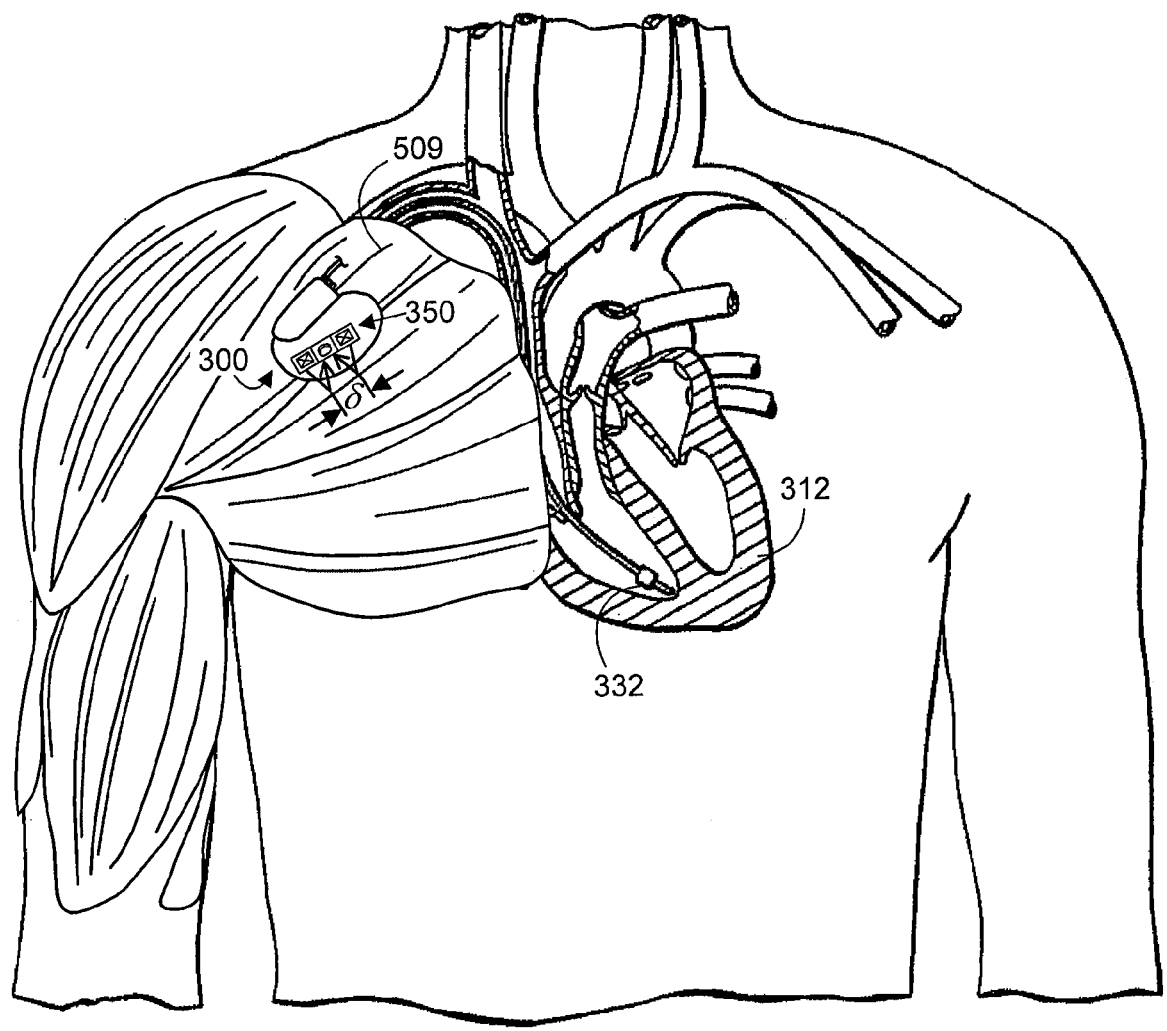
FIG. 5 is a diagram showing a system in accordance with an embodiment of the present invention comprising the device of FIG. 3 implanted within a patient's body and arranged to measure changes in arterial blood volume within peripheral arterial structures at two locations different distances from the central aorta along respective blood flow paths.

In some embodiments described herein a pair of PPG sensors can include their own light sources that share a time multiplexed light detector (e.g., sees FIGS. 3 and 5). In other embodiments, a pair of PPG sensors can include a shared, multiplexed light source and each sensor can include its own light detector, with one of the light detectors being arranged to detect light illuminating a different site from the other light detector. In still further embodiments, each PPG sensor (of a pair of PPG sensors) can include its own light source and its own light detector, each light detector being dedicated to detecting light illuminated by an associated light source (e.g., see FIGS. 6 and 7). In each of these embodiments, one of the PPG sensors is used to obtain a first signal indicative of changes in arterial blood volume at a first site (along one or more peripheral arterial structures of the patient), and the other one of the PPG sensors is used to obtain a second signal indicative of changes in arterial blood volume at a second site (a distance from the first site downstream along an arterial path of the one or more peripheral arterial structures of the patient). A site that is along one or more structures can be located within the one or more structures, adjacent the one or more structures, or otherwise disposed to measure a volume of blood at a known location related to the one or more structures. PPG sensors for use with embodiments of systems in accordance with the present invention need not be limited to the number and arrangement of light sources and light detectors in FIGS. 3-7.

The light sources 352, 354 are multiplexed to output light at different times. The output light is reflected or backscattered by surrounding patient tissue, and reflected/backscattered light is received by the light detector 356. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. A PPG sensor can use a single wavelength of light, or a broad spectrum of many wavelengths. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 350 can be attached to a housing 340 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. Pat. No. 7,653,434, entitled "Autonomous Sensor Modules for Patient Monitoring" (Turcott et al.), which is incorporated herein by reference. It is also possible that the PPG sensor 350 be integrally part of the implantable cardiac stimulation device 300. For example, the PPG sensor 350 can be located within the housing 340 of an ICD (and/or pacemaker) that has a window through which light can be transmitted and detected. In a specific embodiment, the PPG sensor 350 has a titanium frame with light-transparent quartz or sapphire window that can be welded into a corresponding slot cut in the housing of the ICD. This will insure that the ICD enclosure with the welded PPG sensor will maintain a hermetic condition.

Where the PPG sensor 350 is incorporated into or attached to a chronically implantable device 300, the light sources 352, 354 and the light detector 356 can be mounted adjacent to one another on the housing or header of the implantable device, or on the bottom of the device, or at any other location. The light source 352, 354 and the light detector 356 can be placed on the side of the implantable device 300 that, following implantation, faces the chest wall, and are configured such that light cannot pass directly from the source to the detector. The placement on the side of the device 300 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 352, 354 and the light detector 356 can be placed on the face of the device 300 that faces the skin of the patient. Other variations are also possible.

Still referring to FIG. 3, to sense atrial cardiac signals and to provide right atrial chamber stimulation therapy, the device 300 is coupled to an implantable right atrial lead 320 having at least an atrial tip electrode 322, which typically is implanted in the patient's right atrial appendage. To sense left atrial and ventricular cardiac signals and to provide left-chamber pacing therapy, the device 300 is coupled to a "coronary sinus" lead 324 designed for placement in the "coronary sinus region" via the coronary sinus for positioning a distal electrode 326 adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

The device 300 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode 336 will be positioned in the right ventricle and the SVC coil electrode 338 will be positioned in the superior vena cava. Accordingly, the right ventricular lead 330 is capable of receiving cardiac signals and delivering stimulation in the form of pacing and shock therapy to the right ventricle.

FIG. 4 will now be used to provide some exemplary details of the components of the implantable devices 300. Referring now to FIG. 4, the implantable devices 300, and alternative versions thereof, can include a microcontroller 460. As is well known in the art, the microcontroller 460 typically includes a microprocessor, or equivalent control circuitry, and can further include RAM and/or ROM memory, logic and timing circuitry, state machine circuitry and/or I/O circuitry. Typically, the microcontroller 460 includes the ability to process or monitor input signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing and data analysis functions are well known in the art. In specific embodiments of the present invention, the microcontroller 460 performs some or all of the steps associated with determining estimates of central arterial blood pressure (CBP). Additionally, the microcontroller 460 may detect arrhythmias, and select and control delivery of anti-arrhythmia therapy. Still further, in embodiments of the present invention the microcontroller 460 performs some or all of the steps associated with determining estimates of central blood pressure (CBP) as described in embodiments of methods described above.

Representative types of control circuitry that may be used with embodiments of the present invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the pacing device and their interrelationship, see U.S. Pat. No. 4,788,980 (Mann et al.). The '052, '555, '298 and '980 patents are incorporated herein by reference.

Depending on implementation, the device 300 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, if the implantable device is a monitor that does not provide any therapy, it is clear that many of the blocks shown may be eliminated.

The housing 340, shown schematically in FIG. 4, is often referred to as the "can", "case" or "case electrode" and may be programmably selected to act as the return electrode for all "unipolar" modes. The housing 340 may further be used as a return electrode alone or in combination with one or more of the coil electrodes, 128, 136 and 138, for shocking purposes. The housing 340 can further include a connector (not shown) having a plurality of terminals, 442, 444, 446, 448, 452, 454, 456, and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 322.

To achieve left atrial and ventricular sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular tip electrode 326, the left atrial ring electrode 327, and the left atrial coil electrode 328, respectively.

To support right ventricle sensing, pacing and shocking, the connector further includes a right ventricular tip terminal ($V_R$ TIP) 452, a right ventricular ring terminal ($V_R$ RING) 454, a right ventricular shocking terminal ($R_V$COIL) 456, and an SVC shocking terminal (SVC COIL) 458, which are adapted for connection to the right ventricular tip electrode 332, right ventricular ring electrode 334, the RV coil electrode 336, and the SVC coil electrode 338, respectively.

An atrial pulse generator 470 and a ventricular pulse generator 472 generate pacing stimulation pulses for delivery by the right atrial lead 320, the right ventricular lead 330, and/or the coronary sinus lead 324 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuits 482 and ventricular sensing circuits 484 may also be selectively coupled to the right atrial lead 320, coronary sinus lead 324, and the right ventricular lead 330, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, band-pass filtering, and a threshold detection circuit, as known in the art, to selectively sense the cardiac signal of interest. The automatic gain control enables the device 300 to deal effectively with the difficult problem of sensing the low amplitude signal characteristics of atrial or ventricular fibrillation. Such sensing circuits, 482 and 484, can be used to determine cardiac performance values used in the present invention. Alternatively, an automatic sensitivity control circuit may be used to effectively deal with signals of varying amplitude.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 300 includes an arrhythmia detector 462 that utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation) can be classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 462 can perform arrhythmia discrimination, e.g., using measures of arterial blood pressure determined in accordance with embodiments of the present invention. The arrhythmia detector 462 can be implemented within the microcontroller 460, as shown in FIG. 4. Thus, this detector 462 can be implemented by software, firmware, or combinations thereof. It is also possible that all, or portions, of the arrhythmia detector 462 can be implemented using hardware. Further, it is also possible that all, or portions, of the ischemia detector 462 can be implemented separate from the microcontroller 460.

In accordance with an embodiment of the present invention, the implantable device 300 includes a CBP and PBP processor and monitor 467, and a heart failure monitor 468, using the techniques described above. The monitors 467, 468 and 469 can be implemented within the microcontroller 460, as shown in FIG. 4, and can be implemented by software, firmware, or combinations thereof. It is also possible that all, or portions, of the monitors 467, 468 and/or 469 to be implemented using hardware. Further, it is also possible that all, or portions, of the monitors 467, 468 and/or 469 can be implemented separate from the microcontroller 460. The monitors 467, 468 and/or 469 can be used in a closed loop control system to provide an assessment of hemodynamic condition during pacing parameter adjustments, and/or as an assessment of hemodynamic condition during a detected arrhythmia. Such measures of hemodynamic condition can be used when determining which anti-arrhythmia therapy options are appropriate. It is also noted that monitors 467, 468 and/or 469 can be combined into a single monitor, or separated into further blocks.

The implantable device 300 can also include a pacing controller 466, which can adjust a pacing rate and/or pacing intervals based on estimates of CBP, PBP, CPWV and/or PPWV. The pacing controller 466 can be implemented within the microcontroller 460, as shown in FIG. 4. Thus, the pacing controller 466 can be implemented by software, firmware, or combinations thereof. It is also possible that all, or portions, of the pacing controller 466 can be implemented using hardware. Further, it is also possible that all, or portions, of the pacing controller 466 can be implemented separate from the microcontroller 460.

The implantable device can also include a medication pump 403, which can deliver medication to a patient if the patient's fall outside certain thresholds or ranges. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 4, cardiac signals are also applied to the inputs of an analog-to-digital (A/D) data acquisition system 490. The data acquisition system 490 can be configured to acquire various signals, including but not limited to, IEGM and PPG signals, convert the raw analog data into a digital signal, and store the digital signals for later processing and/or telemetric transmission to an external device 402. The data acquisition system 490 can be coupled to the right atrial lead 320, the coronary sinus lead 324, and the right ventricular lead 330 through the switch 474 to sample cardiac signals across any pair of desired electrodes.

The data acquisition system 490 can be coupled to the microcontroller 460, or other detection circuitry, for detecting an evoked response from the heart 312 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

The microcontroller 460 is further coupled to the memory 494 by a suitable data/address bus 496, wherein the programmable operating parameters used by the microcontroller 460 are stored and modified, as required, in order to customize the operation of the implantable device 300 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy. The memory 494 can also store data including information about estimates of CBP, PBP, CPWV and/or PPWV.

The operating parameters of the implantable device 300 may be non-invasively programmed into the memory 494 through a telemetry circuit 401 in telemetric communication with an external device 402, such as a programmer, transtelephonic transceiver, or a diagnostic system analyzer. Likewise, an external device 402 can be used to provide data such as distances through the arterial blood flow path to the controller 460 for calculation of CBP in the CBP and PBP processor and monitor 467. The telemetry circuit 401 can be activated by the microcontroller 460 by a control signal 406. The telemetry circuit 401 advantageously allows intracardiac electrograms and status information relating to the operation of the device 300 (as contained in the microcontroller 460 or memory 494) to be sent to the external device 402 through an established communication link 404. The telemetry circuit can also be use to transmit arterial blood pressure data to the external device 402.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 300 additionally includes a battery 411 which provides operating power to all of the circuits shown in FIG. 4. If the implantable device 300 also employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected.

The implantable device 300 is also shown as including an activity and/or posture sensor 415. Such a sensor 415 can be a simple one dimensional sensor that converts mechanical motion into a detectable electrical signal, such as a back electro magnetic field (BEMF) current or voltage, without requiring any external excitation. Alternatively, the sensor 415 can measure multi-dimensional activity information, such as two or more of acceleration, direction, posture and/or tilt. Examples of multi-dimensional activity sensors include, but are not limited to: the three dimensional accelerometer-based position sensor disclosed in U.S. Pat. No. 6,658,292 to Kroll et al., which is incorporated herein by reference; the AC/DC multi-axis accelerometer disclosed in U.S. Pat. No. 6,466,821 to Pianca et al., which in incorporated herein by reference; and the commercially available precision dual-axis accelerometer model ADXL203 and three-axis accelerometer model ADXL346, both available from Analog Devices of Norwood, Mass.

The implantable device 300 can also include a magnet detection circuitry (not shown), coupled to the microcontroller 460. It is the purpose of the magnet detection circuitry to detect when a magnet is placed over the implantable device 300, which magnet may be used by a clinician to perform various test functions of the implantable device 300 and/or to signal the microcontroller 460 that the external programmer 402 is in place to receive or transmit data to the microcontroller 460 through the telemetry circuits 401.

As further shown in FIG. 4, the device 300 is also shown as having an impedance measuring and processing circuit 413 which is enabled by the microcontroller 460 via a control signal 414 and can be used for obtaining many types of bodily and intracardiac impedances, including a network of single- or multi-vector impedance measurements. Such impedance measurements can be used, e.g., for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 413 may be coupled to the switch 474 so that any desired electrodes may be used, and networks of vectors can be selected. The impedance measuring circuit 413, when measuring impedance using implanted electrodes that are remote from the patient's heart, can be used to obtain impedance plethysmography (IPG) signals.

In the case where the implantable device 300 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (11 to 40 Joules), as controlled by the microcontroller 460. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 340 may act as an active electrode in combination with the RV electrode 336, or as part of a split electrical vector using the SVC coil electrode 338 or the left atrial coil electrode 328 (i.e., using the RV electrode as a common electrode).

The above described implantable device 300 was described as an exemplary pacing device. One or ordinary skill in the art would understand that embodiments of the present invention can be used with alternative types of implantable devices. Accordingly, embodiments of the present invention should not be limited to use only with the above described device.

FIG. 5 illustrates an embodiment of a system in accordance with the present invention comprising the device 300 of FIG. 3 implanted along a patient's pectoral muscle 509. For the purposes of description, the housing of the device 300 and internal components are transparent so as to show a PPG sensor 350 mounted on a portion of the surface of the device 300 contacting or otherwise facing the pectoral muscle 509. The pectoral muscle has a generally fan-like shape, and the arterioles and/or capillaries that deliver blood to the muscle run along muscle fascicles. The light sources (352, 354 in FIG. 3) of the PPG sensor 350 are arranged generally along the arterioles and/or capillaries of the pectoral muscle, preferably in a location where the muscles fascicles extend approximately linearly so that the known distance between the light sources can predictably approximate the distance along the blood flow path between the sites illuminated by the light sources. As noted above, the light sources need not necessarily illuminate arterial structures in the same muscle fascicles. Arterial structures in the neighboring muscle fascicles can be assumed to have approximately the same blood flow characteristics.

Figure 6:
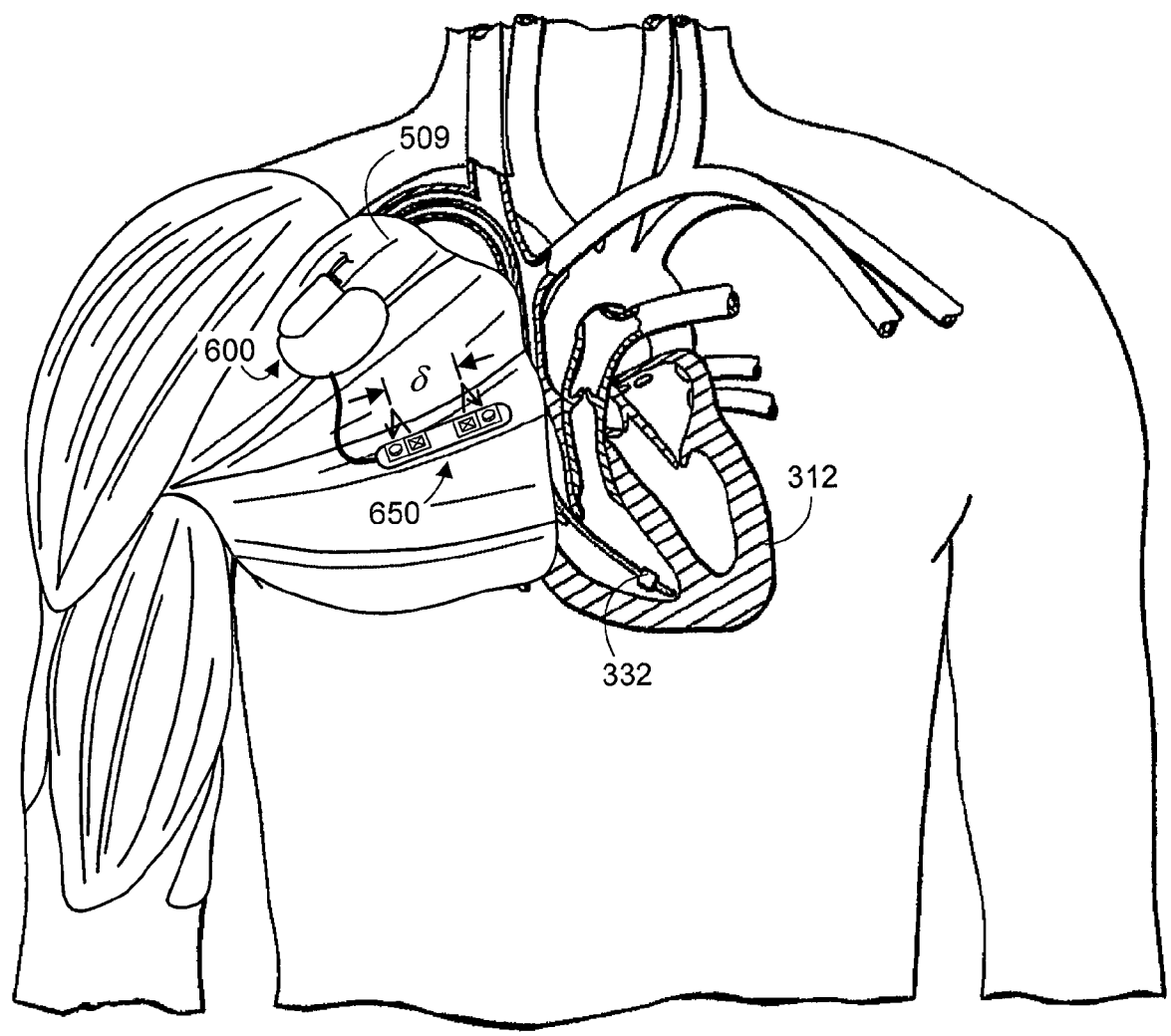
FIG. 6 is a diagram showing an alternative embodiment of a system in accordance with the present invention for determining central arterial blood pressure, the system including an implantable stimulation device connected by wire with a separate PPG sensor subcutaneously implanted and arranged to measure changes in arterial blood volume within peripheral arterial structures at two locations different distances from the central aorta along respective blood flow paths.
Figure 7:
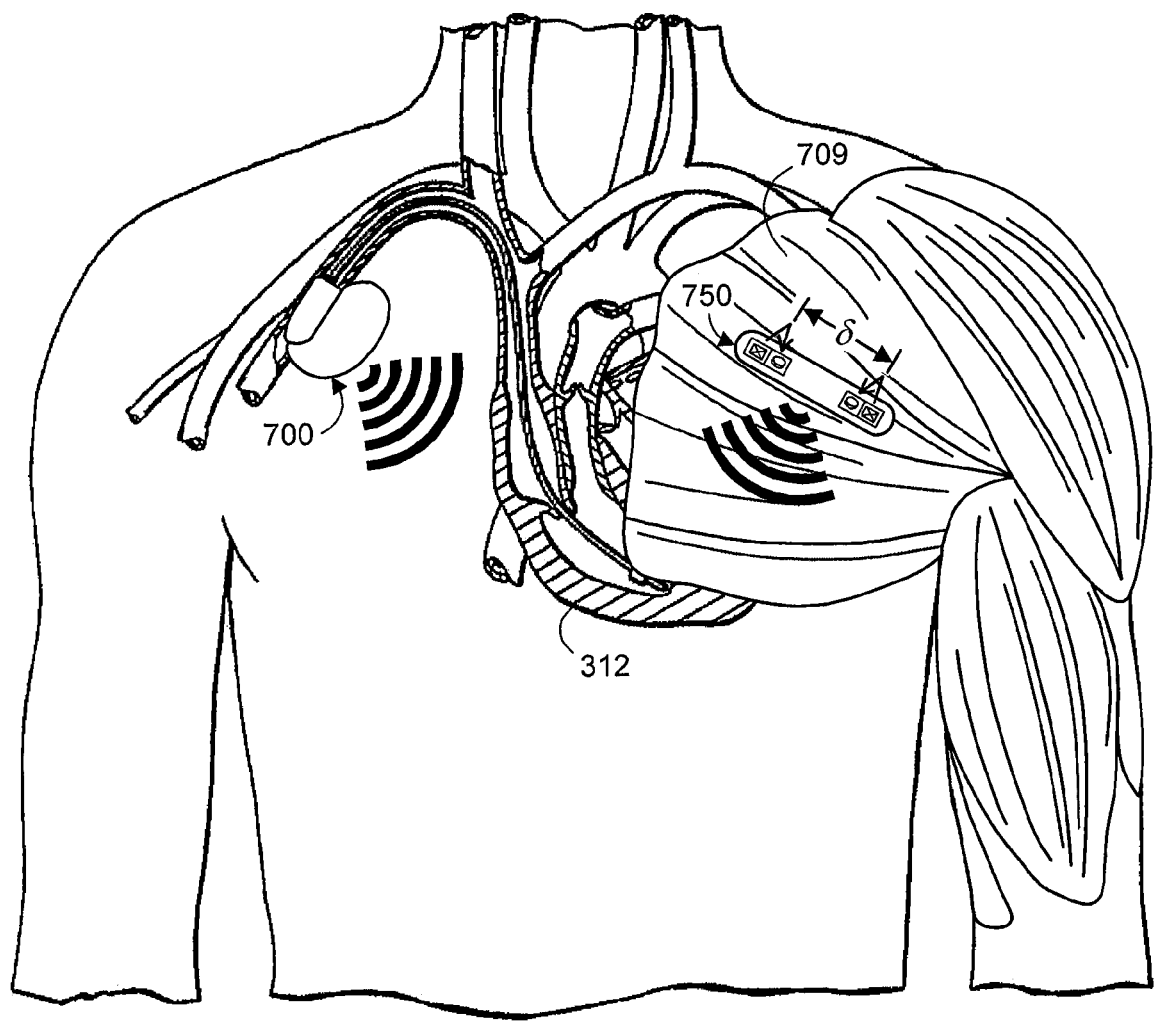
FIG. 7 is a diagram showing a further embodiment of a system in accordance with the present invention for determining central arterial blood pressure, the system including an implantable stimulation device wirelessly connected with a separate PPG sensor subcutaneously implanted and arranged to measure changes in arterial blood volume within peripheral arterial structures at two locations different distances from the central aorta along respective blood flow paths.

Referring to FIGS. 6 and 7, in alternative embodiments, the PPG sensor 650, 750 (or other plethysmography sensor) can be remote from the housing of the device 600, 700 but communicates with the electronics in the device housing via one or more wires, optical fibers, or wirelessly (e.g., using telemetry, RF signals and/or using body fluid as a communication bus medium). Such embodiments enable an obtained PPG signal to be indicative of changes in arterial blood volume at a location remote from the patient's heart, where such location is also remote from the device housing. As shown, the PPG sensors can be arranged to measure arterioles in the left pectoral 709 or the right pectoral 509. Further, a PPG sensor 650, 750 separate from the housing of the device 600, 700 can measure sites distanced further from each other along the blood flow path. Increasing a distance between sites can potentially improve PAT estimates, provided that the accuracy of the longer distance when compared with the actual blood flow path distance is not unacceptably reduced due to non-linearity of the blood flow path. If desired, multiple PPG signals can be obtained, e.g., using multiple PPG sensors at different locations.

In another embodiment, optical fibers can be used to transmit light into and detect light from tissue that is remote from the device housing, even though the light source and light detector are located within or adjacent the device housing. This embodiment enables an obtained PPG signal to be indicative of changes in arterial blood volume at a location remote from the patient's heart, where such location is remote from the device housing, even though the light source and light detector are not remote from the housing. The distal end of the optical fiber(s) associated with the light source can be generally parallel to the distal end of the optical fiber(s) associated with the light detector, so that the light detector detects the portion of light reflected from tissue. Alternatively, the distal end of the optical fiber(s) associated with the light source can generally face the distal end of the optical fiber(s) associated with the light detector, with tissue therebetween, so that the light detector detects the portion of light transmitted through (as opposed to reflected from) the tissue therebetween.

In an embodiment, a PPG sensor can be within or attached to a lead that may extend from a main device housing. Accordingly, in this embodiment, a housing of the sensor module is sized to fit within the implantable lead. For example, the PPG sensor can be located proximal from the distal tip of the lead so that the PPG sensor is sufficiently remote from the heart that variations in pulse transmission time are detectable and meaningful. The portion of the lead that is adjacent to a window of the PPG sensor module, where light is to exit and enter, should allow the light to pass in and out of the sensor. Thus, the lead may be transparent, or include its own window, opening, or the like. The lead can including tines for attaching the lead in its desired position, but may include any other type of fixation means (e.g., a pigtail shaped fixation means), or none at all. The lead can also have a suture sleeve, that enables the lead to be sutured to patient tissue. Additional details of a lead that includes an optical sensor that can be used to produce a PPG signal are provided in U.S. patent application Ser. No. 11/231,555, entitled "Improved Multi-Wavelength Implantable Oximeter Sensor" (Poore), filed Sep. 20, 2005, now U.S. Pat. No. 7,660,616; and U.S. patent application Ser. No. 11/282,198, entitled "Implantable Device with a Calibration Photodetector" (Poore), filed Nov. 17, 2005, now U.S. Pat. No. 7,840,246.

The implantable PPG sensor obtains a PPG signal that after filtering is similar to signal 132 shown in FIGS. 1A and 1B that pulsates over the cardiac cycle. Modulation of the signal occurs because arteries distend as the pressure wave created by the heart's pumping mechanism reaches the sensor site. Such a signal can be filtered and/or amplified as appropriate, e.g., to remove respiratory affects on the signal, and the like. Additionally, the signal can be digitized using an analog to digital converter.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals. Further, as mentioned above, electrodes of the various leads can be used to obtain an IPG signal, and the IPG signal can be used in place of the PPG signal.

In specific embodiments, the plethysmography signal can be produced using non-radiant methods and devices, including, but not limited to mechanical strain, electrical impedance, or pressure. More specifically, rather than using a PPG sensor that includes a light source and detector, the implanted plethysmography sensor can include a strain gauge, a linear displacement sensor, or an ultrasound transducer, each of which is known in the art. Alternatively, an impedance plethysmography sensor, which is also known in the art, can be used. Details of exemplary implantable sensors that produce an impedance plethysmography signals are disclosed, e.g., in U.S. Pat. Nos. 4,674,518; 4,686,987; and 5,334,222 (all to Salo), which are incorporated herein by reference. Regardless of the type of plethysmography signals being obtained, one of the plethysmography signals should be indicative of changes in arterial blood volume at one site, and the other plethysmography signal should be indicative of changes in arterial blood volume at another location a distance from the first site downstream along an arterial path of the peripheral arterial structure of the patient.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 2. Further, it is possible to change the order of some of the steps shown in FIG. 2, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with an implantable cardiac system, a method for estimating a patient's central arterial blood pressure (CBP), the method comprising:
   (a) using an implanted sensor at a first site to obtain a first signal indicative of changes in arterial blood volume at the first site, the first site being along one or more peripheral arterial structures of the patient;
   (b) using an implanted sensor at a second site to obtain a second signal indicative of changes in arterial blood volume at the second site, the second site being a distance from the first site downstream along an arterial path of the one or more peripheral arterial structures of the patient;
   (c) using implanted electrodes to obtain a signal indicative of electrical activity of the patient's heart;
   (d) determining, using a processor, a time $t_1$ from a predetermined feature of the signal indicative of electrical activity of the patient's heart to a predetermined feature of one of the first and second signals, the time $t_1$ being a first pulse arrival time ($PAT_1$) indicative of how long it takes a pulse wave to travel from the patient's aorta to one of the first and second sites;
   (e) determining, using the processor, a time $t_2$ from a predetermined feature of the signal indicative of electrical activity of the patient's heart to a predetermined feature of the other of the first and second signals, the time $t_2$ being a second pulse arrival time ($PAT_2$) indicative of how long it takes a pulse wave to travel from the patient's aorta to the other of the first and second sites; and
   (f) estimating, using the processor, the patient's central arterial blood pressure (CBP) based on $PAT_1$ and $PAT_2$, with step (f) further comprising;
      (f.1) estimating a peripheral pulse wave velocity (PPWV), indicative of a pulse wave velocity between the first and second sites, based on $PAT_1$ and $PAT_2$ and the distance from the first site to the second site;
      (f.2) estimating a central pulse wave velocity (CPWV), indicative of a pulse wave velocity proximal the patient's aorta, based on the first pulse arrival time ($PAT_1$) and the peripheral pulse wave velocity (PPWV), wherein the CPWV is estimated using the following equation:

$$v_{cpw} \approx \frac{v_{ppw} * d_c}{v_{ppw} * PAT_x - d_p}$$

where
   $v_{cpw}$ is the estimated CPWV,
   $v_{ppw}$ is the estimated PPWV,
   $PAT_x$ is one of $PAT_1$ and $PAT_2$,
   $d_c$ is a distance traveled in central arterial structures, and
   $d_p$ is a distance traveled in peripheral arterial structures to the measurement location of $PAT_x$;

(f.3) estimating the patient's CBP based on the estimated CPWV; and (g) delivering at least one of heart chamber stimulation and heart shock therapy to a patient's heart, with the delivery of the at least one of heart chamber stimulation and heart shock therapy based, at least in part, upon the estimated CBP.

2. The method of claim 1, wherein step (f.3) comprises estimating the patient's CBP based on the square of the CPWV.

3. The method of claim 2, wherein step (f.3) comprises estimating the patient's CBP using the equation:

$$CBP \approx k1 * v_{cpw}^2 + k2$$

where
CBP is the estimated central arterial blood pressure,
$v_{cpw}$ is the estimated CPWV,
k1 is a constant indicative of a linearized scaling factor between pulse wave velocity and blood pressure, and
k2 is a constant indicative of an offset used with the scaling factor to make a linear approximation of blood pressure based on pulse wave velocity.

4. The method of claim 3, further comprising determining the constants k1 and k2 by:
while the patient is in an initial position
using a secondary technique to measure initial peripheral blood pressure of the patient,
using the implanted sensor at the first site to obtain a first calibration signal indicative of a change in arterial blood volume, and
using the implanted sensor at the second site to obtain a second calibration signal indicative of a change in blood volume;
while the patient is in a secondary position
using a secondary technique to measure a secondary peripheral blood pressure of the patient,
using the implanted sensor at the first site to obtain a third calibration signal indicative of a change in arterial blood volume, and
using the implanted sensor at the second site to obtain a fourth calibration signal indicative of a change in blood volume; and
calculating the constants k1 and k2 using the first calibration signal, the second calibration signal, the third calibration signal, the fourth calibration signal, the initial peripheral blood pressure, the secondary peripheral blood pressure, and the distance from the first site to the second site.

5. The method of claim 1, further comprising:
estimating the patient's peripheral arterial blood pressure (PBP) based on the PPWV.

6. The method of claim 5, wherein estimating the patient's PBP comprises using the equation:

$$PBP \approx k3 * v_{ppw}^2 + k4$$

where
PBP is the estimated peripheral arterial blood pressure,
$v_{ppw}$ is the estimated PPWV,
k3 is a constant indicative of a linearized scaling factor between pulse wave velocity and blood pressure (accounting for blood density, blood volume and vascular compliance), and
k4 is a constant indicative of an offset used with the scaling factor to make a linear approximation of blood pressure based on pulse wave velocity.

7. The method of claim 6, further comprising determining the constants k3 and k4 by:
while the patient is in an initial position
using a secondary technique to measure initial peripheral blood pressure of the patient,
using the implanted sensor at the first site to obtain a first calibration signal indicative of a change in arterial blood volume, and
using the implanted sensor at the second site to obtain a second calibration signal indicative of a change in blood volume;
while the patient is in a secondary position
using a secondary technique to measure a secondary peripheral blood pressure of the patient,
using the implanted sensor at the first site to obtain a third calibration signal indicative of a change in arterial blood volume, and
using the implanted sensor at the second site to obtain a fourth calibration signal indicative of a change in blood volume; and
calculating the constants k3 and k4 using the first calibration signal, the second calibration signal, the third calibration signal, the fourth calibration signal, the initial peripheral blood pressure, the secondary peripheral blood pressure, and the distance from the first site to the second site.

8. The method of claim 1, wherein:
step (a) comprises using an implanted optical sensor at the first site to obtain a first photoplethysmography (PPG) signal indicative of changes in arterial blood volume at the first site;
step (b) comprises using an implanted optical sensor at the second site to obtain a second photoplethysmography (PPG) signal indicative of changes in arterial blood volume at the second site; and
step (c) comprises using implanted electrodes to obtain an intracardiac electrogram (IEGM) signal indicative of electrical activity of the patient's heart.

9. The method of claim 8, wherein in steps (d) and (e):
the predetermined features of the first and second PPG signals are selected from the group consisting of
the minimum amplitude of the PPG signal,
the maximum upward slope of the PPG signal,
the maximum amplitude of the PPG signal,
the maximum downward slope of the PPG signal prior to the dicrotic notch,
the dicrotic notch of the PPG signal, and
the maximum downward slope of the PPG signal following the dicrotic notch; and
the predetermined feature of the IEGM signal is selected from the group consisting of
a Q-wave,
a R-wave, and
a QRS complex.

10. For use with an implantable cardiac system, a method for estimating a patient's central arterial blood pressure (CBP), the method comprising:
(a) using an implanted sensor at a first site to obtain a first signal indicative of changes in arterial blood volume at the first site, the first site being along one or more peripheral arterial structures of the patient;
(b) using an implanted sensor at a second site to obtain a second signal indicative of changes in arterial blood volume at the second site, the second site being a distance from the first site downstream along an arterial path of the one or more peripheral arterial structures of the patient;

(c) using implanted electrodes to obtain a signal indicative of electrical activity of the patient's heart;
(d) determining, using a processor, a time $t_1$ from a predetermined feature of the signal indicative of electrical activity of the patient's heart to a predetermined feature of one of the first and second signals, the time $t_1$ being a first pulse arrival time ($PAT_1$) indicative of how long it takes a pulse wave to travel from the patient's aorta to one of the first and second sites;
(e) determining, using the processor, a time $t_2$ from a predetermined feature of the signal indicative of electrical activity of the patient's heart to a predetermined feature of the other of the first and second signals, the time $t_2$ being a second pulse arrival time ($PAT_2$) indicative of how long it takes a pulse wave to travel from the patient's aorta to the other of the first and second sites; and
(f) estimating, using the processor, the patient's central arterial blood pressure (CBP) based on $PAT_1$ and $PAT_2$, with step (f) further comprising;
 (f.1) estimating a peripheral pulse wave velocity (PPWV), indicative of a pulse wave velocity between the first and second sites, based on $PAT_1$ and $PAT_2$ and the distance from the first site to the second site;
 (f.2) estimating a central pulse wave velocity (CPWV), indicative of a pulse wave velocity proximal the patient's aorta, based on $PAT_1$ and the PPWV;
 (f.3) estimating the patient's CBP based on the estimated square of the CPWV and using the equation:

$$CBP \approx k1 * v_{cpw}^2 + k2$$

where
 $v_{cpw}$ is the estimated CPWV,
 k1 is a constant indicative of a linearized scaling factor between pulse wave velocity and blood pressure, and
 k2 is a constant indicative of an offset used with the scaling factor to make a linear approximation of blood pressure based on pulse wave velocity;
determining the constants k1 and k2 by:
while the patient is in an initial position
using a secondary technique to measure initial peripheral blood pressure of the patient,
using the implanted sensor at the first site to obtain a first calibration signal indicative of a change in arterial blood volume, and
using the implanted sensor at the second site to obtain a second calibration signal indicative of a change in blood volume;
while the patient is in a secondary position
using a secondary technique to measure a secondary peripheral blood pressure of the patient,
using the implanted sensor at the first site to obtain a third calibration signal indicative of a change in arterial blood volume, and
using the implanted sensor at the second site to obtain a fourth calibration signal indicative of a change in blood volume;
calculating the constants k1 and k2 using the first calibration signal, the second calibration signal, the third calibration signal, the fourth calibration signal, the initial peripheral blood pressure, the secondary peripheral blood pressure, and the distance from the first site to the second site; and
(g) delivering at least one of heart chamber stimulation and heart shock therapy to a patient's heart, with the delivery of the at least one of heart chamber stimulation and heart shock therapy based, at least in part, upon the estimated CBP.

11. The method of claim 10, further comprising:
estimating the patient's peripheral arterial blood pressure (PBP) based on the PPWV.

12. The method of claim 11, wherein estimating the patient's PBP comprises using the equation:

$$PBP \approx k3 * v_{ppw}^2 + k4$$

where
 PBP is the estimated peripheral arterial blood pressure,
 $v_{ppw}$ is the estimated PPWV,
 k3 is a constant indicative of a linearized scaling factor between pulse wave velocity and blood pressure (accounting for blood density, blood volume and vascular compliance), and
 k4 is a constant indicative of an offset used with the scaling factor to make a linear approximation of blood pressure based on pulse wave velocity.

13. The method of claim 12, further comprising determining the constants k3 and k4 by:
while the patient is in an initial position
using a secondary technique to measure initial peripheral blood pressure of the patient,
using the implanted sensor at the first site to obtain a first calibration signal indicative of a change in arterial blood volume, and
using the implanted sensor at the second site to obtain a second calibration signal indicative of a change in blood volume;
while the patient is in a secondary position
using a secondary technique to measure a secondary peripheral blood pressure of the patient,
using the implanted sensor at the first site to obtain a third calibration signal indicative of a change in arterial blood volume, and
using the implanted sensor at the second site to obtain a fourth calibration signal indicative of a change in blood volume; and
calculating the constants k3 and k4 using the first calibration signal, the second calibration signal, the third calibration signal, the fourth calibration signal, the initial peripheral blood pressure, the secondary peripheral blood pressure, and the distance from the first site to the second site.

14. The method of claim 10, wherein:
step (a) comprises using an implanted optical sensor at the first site to obtain a first photoplethysmography (PPG) signal indicative of changes in arterial blood volume at the first site;
step (b) comprises using an implanted optical sensor at the second site to obtain a second photoplethysmography (PPG) signal indicative of changes in arterial blood volume at the second site; and
step (c) comprises using implanted electrodes to obtain an intracardiac electrogram (IEGM) signal indicative of electrical activity of the patient's heart.

15. The method of claim 14, wherein in steps (d) and (e):
the predetermined features of the first and second PPG signals are selected from the group consisting of
the minimum amplitude of the PPG signal,
the maximum upward slope of the PPG signal,
the maximum amplitude of the PPG signal,
the maximum downward slope of the PPG signal prior to the dicrotic notch,
the dicrotic notch of the PPG signal, and
the maximum downward slope of the PPG signal following the dicrotic notch; and the predetermined feature of the IEGM signal is selected from the group consisting of
a Q-wave,
a R-wave, and
a QRS complex.

16. For use with an implantable cardiac system, a method for estimating a patient's central arterial blood pressure (CBP), the method comprising:
(a) using an implanted sensor at a first site to obtain a first signal indicative of changes in arterial blood volume at the first site, the first site being along one or more peripheral arterial structures of the patient;
(b) using an implanted sensor at a second site to obtain a second signal indicative of changes in arterial blood volume at the second site, the second site being a distance from the first site downstream along an arterial path of the one or more peripheral arterial structures of the patient;
(c) using implanted electrodes to obtain a signal indicative of electrical activity of the patient's heart;
(d) determining, using a processor, a time $t_1$ from a predetermined feature of the signal indicative of electrical activity of the patient's heart to a predetermined feature of one of the first and second signals, the time $t_1$ being a first pulse arrival time ($PAT_1$) indicative of how long it takes a pulse wave to travel from the patient's aorta to one of the first and second sites;
(e) determining, using the processor, a time $t_2$ from a predetermined feature of the signal indicative of electrical activity of the patient's heart to a predetermined feature of the other of the first and second signals, the time $t_2$ being a second pulse arrival time ($PAT_2$) indicative of how long it takes a pulse wave to travel from the patient's aorta to the other of the first and second sites; and
(f) estimating, using the processor, the patient's central arterial blood pressure (CBP) based on $PAT_1$ and $PAT_2$ with step (f) further comprising;
(f.1) estimating a peripheral pulse wave velocity (PPWV), indicative of a pulse wave velocity between the first and second sites, based on $PAT_1$ and $PAT_2$ and the distance from the first site to the second site;
(f.2) estimating a central pulse wave velocity (CPWV), indicative of a pulse wave velocity proximal the patient's aorta, based on the first pulse arrival time ($PAT_1$) and the peripheral pulse wave velocity (PPWV);
(f.3) estimating the patient's CBP based on the estimated CPWV;
(g) estimating, using the processor, the patient's peripheral arterial blood pressure (PBP) based on the PPWV and using the equation:

$$PBP \approx k3 * v_{ppw}^2 + k4$$

where
PBP is the estimated peripheral arterial blood pressure,
$v_{ppw}$ is the estimated PPWV,
k3 is a constant indicative of a linearized scaling factor between pulse wave velocity and blood pressure (accounting for blood density, blood volume and vascular compliance),
k4 is a constant indicative of an offset used with the scaling factor to make a linear approximation of blood pressure based on pulse wave velocity;
determining, using the processor, the constants k3 and k4 by:
while the patient is in an initial position
using a secondary technique to measure initial peripheral blood pressure of the patient,
using the implanted sensor at the first site to obtain a first calibration signal indicative of a change in arterial blood volume, and
using the implanted sensor at the second site to obtain a second calibration signal indicative of a change in blood volume;
while the patient is in a secondary position
using a secondary technique to measure a secondary peripheral blood pressure of the patient,
using the implanted sensor at the first site to obtain a third calibration signal indicative of a change in arterial blood volume, and
using the implanted sensor at the second site to obtain a fourth calibration signal indicative of a change in blood volume;
calculating the constants k3 and k4 using the first calibration signal, the second calibration signal, the third calibration signal, the fourth calibration signal, the initial peripheral blood pressure, the secondary peripheral blood pressure, and the distance from the first site to the second site; and
delivering at least one of heart chamber stimulation and heart shock therapy to a patient's heart, with the delivery of the at least one of heart chamber stimulation and heart shock therapy based, at least in part, upon the estimated CBP.

17. The method of claim 16, wherein step (f.2) comprises estimating the CPWV using the following equation:

$$v_{cpw} \approx \frac{v_{ppw} * d_c}{v_{ppw} * PAT_x - d_p}$$

where
$v_{cpw}$ is the estimated CPWV,
$v_{ppw}$ is the estimated PPWV,
$PAT_x$ is one of $PAT_1$ and $PAT_2$,
$d_c$ is a distance traveled in central arterial structures, and
$d_p$ is a distance traveled in peripheral arterial structures to the measurement location of $PAT_x$.

18. The method of claim 16, wherein:
step (a) comprises using an implanted optical sensor at the first site to obtain a first photoplethysmography (PPG) signal indicative of changes in arterial blood volume at the first site;
step (b) comprises using an implanted optical sensor at the second site to obtain a second photoplethysmography (PPG) signal indicative of changes in arterial blood volume at the second site; and
step (c) comprises using implanted electrodes to obtain an intracardiac electrogram (IEGM) signal indicative of electrical activity of the patient's heart.

19. The method of claim 18, wherein in steps (d) and (e):
the predetermined features of the first and second PPG signals are selected from the group consisting of
the minimum amplitude of the PPG signal,
the maximum upward slope of the PPG signal,
the maximum amplitude of the PPG signal,
the maximum downward slope of the PPG signal prior to the dicrotic notch,
the dicrotic notch of the PPG signal, and
the maximum downward slope of the PPG signal following the dicrotic notch; and
the predetermined feature of the IEGM signal is selected from the group consisting of
a Q-wave,
a R-wave, and
a QRS complex.

* * * * *